(12) United States Patent
Lambrecht et al.

(10) Patent No.: US 7,098,347 B2
(45) Date of Patent: Aug. 29, 2006

(54) PROCESS FOR THE PREPARATION OF 1-HYDROPEROXY-16-OXABICYCLO [10.4.0]HEXADECANE

(75) Inventors: Stefan Lambrecht, Holzminden (DE); Werner Marks, Brevörde (DE); Hans-Juergen Topp, Holzminden (DE); Norbert Richter, Beverungen (DE); Walter Kuhn, Holzminden (DE)

(73) Assignee: symrise GmbH & Co. KG, Holmzinden (DE)

( * ) Notice: Subject to any disclaimer, the term of this patent is extended or adjusted under 35 U.S.C. 154(b) by 0 days.

(21) Appl. No.: 10/939,012

(22) Filed: Sep. 10, 2004

(65) Prior Publication Data

US 2005/0085536 A1     Apr. 21, 2005

(30) Foreign Application Priority Data

Oct. 16, 2003  (DE) ................. 103 48 168

(51) Int. Cl.
  *C07D 311/94*  (2006.01)
  *C07D 313/00*  (2006.01)
  *A61Q 13/00*   (2006.01)
(52) U.S. Cl. ...................... 549/266; 549/396
(58) Field of Classification Search ............... 549/266, 549/396
  See application file for complete search history.

(56) References Cited

U.S. PATENT DOCUMENTS

| | | | |
|---|---|---|---|
| 3,856,815 A | 12/1974 | Hopp | |
| 3,890,353 A * | 6/1975 | Becker | ................ 549/266 |
| 5,266,559 A | 11/1993 | Fankhauser | |
| 2004/0030194 A1 | 2/2004 | Esser | |

FOREIGN PATENT DOCUMENTS

| | | |
|---|---|---|
| EP | 0 424 787 A | 5/1991 |
| EP | 1 375 491 A1 | 1/2004 |

OTHER PUBLICATIONS

Chemical Abstracts 55:141087 (1961).*
Roempp: "Chemie Lexicon, 10. Auflage" 1998, Georg Thieme Verlag, Stuttgart, DE, XP002318781.

* cited by examiner

*Primary Examiner*—Bernard Dentz
(74) *Attorney, Agent, or Firm*—Akerman Senterfitt; Stephan A. Pendorf

(57) ABSTRACT

Process for the preparation of 1-hydroperoxy-16-oxabicyclo [10.4.0]hexadecane (DDP-OOH), wherein 13-oxabicyclo [10.4.0]hexadec-1(12)-ene (DDP) and hydrogen peroxide are reacted in a diluent in the presence of a strong acid, the diluent has a pKa value of greater than or equal to 4.5 and the strong acid has a pKa value of less than or equal to 1.5, wherein after the reaction has taken place, the strong acid is neutralized with at least 0.9 molar equivalent of a base.

18 Claims, No Drawings

PROCESS FOR THE PREPARATION OF 1-HYDROPEROXY-16-OXABICYCLO [10.4.0]HEXADECANE

FIELD OF THE INVENTION

The present invention relates to a process for the preparation of 1-hydroperoxy-16-oxabicyclo[10.4.0]hexadecane (DDP hydroperoxide, DDP-OOH) starting from 13-oxabicyclo[10.4.0]hexadec-1(12)-ene (DDP), and a process for the preparation of 11(12)-pentadecen-15-olide from the DDP-OOH prepared in this way. The compounds 11-pentadecen-15-olide and 12-pentadecen-15-olide and mixtures thereof (11(12)-pentadecen-15-olides) are known and important musk aromas. Both the particular (E) and (Z) forms and mixtures thereof are of interest in terms of smell. EP-A 424 787 describes the smell characteristics of these substances. It is also widely known that 15-pentadecanolide (15-hydroxypentadecanoic acid lactone), which is also used as a musk aroma, can be obtained from 11(12)-pentadecen-15-olides by means of hydrogenation.

BACKGROUND TO THE INVENTION

The preparation of 11(12)-pentadecen-15-olides advantageously proceeds starting from 13-oxabicyclo[10.4.0]hexadec-1(12)-ene (DDP). 1-Hydroperoxy-16-oxabicyclo [10.4.0]hexadecane (DDP hydroperoxide, DDP-OOH) is obtained by acid-catalyzed addition of hydrogen peroxide on to DDP. Cleavage of the DDP-OOH to form the macrocyclic ring is to be regarded as the second step in the synthesis to give the 11(12)-pentadecen-15-olides. This cleavage is usually carried out in the presence of catalysts such as $Cu(OAc)_2$ and, where appropriate, $FeSO_4$. If this reaction stage is carried out purely by means of heat, the reaction product contains considerable amounts of the saturated compound 15-pentadecanolide, which is indeed a musk aroma, but has different smell characteristics to the 11(12)-pentadecen-15-olides and should therefore be formed in only the smallest possible amounts. Furthermore, the high formation of residues (e.g. distillation bottom product) is a disadvantage of the cleavage purely by means of heat.

DDP is conventionally obtained by acid-catalyzed cyclization, with splitting off of water, of 2-(3-hydroxypropyl)-1-cyclododecanone (OCP), which in turn can be synthesized by free-radical addition of allyl alcohol on to cyclododecanone (e.g. in DE-OS 2 136 496).

The process for the preparation of the 11(12)-pentadecen-15-olides can be illustrated by the following equation:

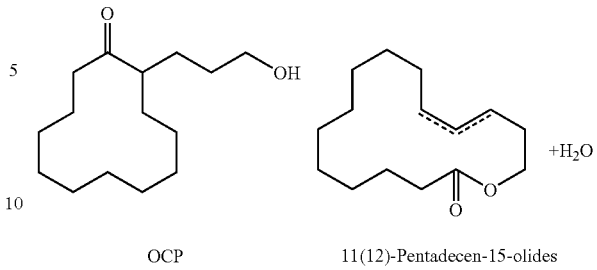

In EP-A 424 787, OCP was homogenized in 4.6 weight equivalents of glacial acetic acid at room temperature, a cold 25% strength by weight aqueous solution of sulfuric acid (about 51 mol % (about 21 wt. %), based on the OCP) was added and the reaction mixture was then cooled to 0° C. Thereafter, 1.65 molar equivalents of $H_2O_2$ (70% strength by wt. solution) were added, the temperature rising to 7° C. After a short after-reaction time, the solid formed (DDP-OOH) was filtered off and this was washed with water and aqueous $NaHCO_3$ solution and dried; the yield was 80%.

Cleavage of the DDP-OOH was carried out by introducing the DDP-OOH in portions into a saturated solution of $Cu(OAc)_2$ in methanol (prepared from about 94 mol % $Cu(OAc)_2$ and 12.3 parts by weight of methanol, based on the DDP-OOH; the concentration of DDP-OOH in this amount of methanol was about 0.25 mol/l). The addition of 2 portions of $FeSO_4$ (in each case just about 20 mol %, based on the DDP-OOH) and stirring overnight at room temperature followed. For working up, the mixture was added to saturated aqueous NaCl solution and extracted with diisopropyl ether and this extract was washed with saturated aqueous $NaHCO_3$ solution and saturated aqueous NaCl solution. After drying and fractional distillation, 73% of theory of 11(12)-pentadecen-15-olides, which also contained 8% of 15-pentadecanolide, was obtained.

In Russ. Chem. Bull. 1998, 47, 1166–1169, DDP was initially introduced into 5.2 weight equivalents of glacial acetic acid at 0° C., and a mixture comprising a 50% strength by wt. aqueous solution of sulfuric acid (about 26 mol % (=11 wt. %), based on the DDP) and 30% strength by wt. hydrogen peroxide (about 1.89 molar equivalents) was added. After a short after-reaction time, the solid formed (DDP-OOH) was filtered off and this was washed with a 50% strength acetic acid solution (80 wt. %, based on the DDP) and then several times with water (4 washing operations with in each case 2 parts by weight of water, based on the DDP) until the wash water was neutral. After drying of the solid, 85% of theory of DDP-OOH, which had a purity of 96%, was obtained.

Cleavage of the DDP-OOH was carried out by metering a suspension of 1 portion of DDP-OOH and about 3.8 portions by weight of 4-methylpentan-2-one (MIBK) into a boiling solution of $Cu(OAc)_2$ in about 3.8 portions by weight of MIBK (based on the DDP-OOH) over a relatively long period of time. The amount of $Cu(OAc)_2$ was varied in the range from 0.15 to 7.0 mol %, based on the DDP-OOH, according to the authors the optimum being 5 mol % $Cu(OAc)_2$. After 3 hours of after-reaction time at the boiling point, the reaction mixture was cooled and freed from the copper salts which had precipitated out. The filtrate was washed with hot water (2 washing operations with in each case 7.7 weight equivalents of water, based on the DDP- OOH) and concentrated. Using 5 mol % Cu(OAc)$_2$ a crude yield of 11(12)-pentadecen-15-olides of 96.5% of theory was obtained.

Disadvantages of these processes are, in particular, the precipitating out of elemental copper and/or insoluble copper compounds under the reaction conditions of the cleavage of DDP-OOH and the large amounts of reagents and auxiliary substances used in the reactions. Further disadvantages which are to be mentioned are, for example, the many, in some cases expensive process steps and the unsatisfactory space/time yield. Washing of the DDP-OOH crystals, in some cases until the wash water is neutral, not only is expensive and environmentally unfriendly, but also makes clear that residues of acid in the DDP-OOH are to be avoided for the subsequent stage of fragmenting. The isolation of the DDP hydroperoxide, which not only is expensive, but also presents safety problems, since hydroperoxides have a high risk potential, is a disadvantage in particular.

The known synthesis processes are therefore unsuitable for an industrial reaction. An industrial process which provides 11(12)-pentadecen-15-olides in a simple and inexpensive manner is therefore of great economic interest.

With the present invention, it is possible to overcome the disadvantages mentioned and to provide an industrially favourable process. The process according to the invention is particularly suitable for use on an industrial scale.

SUMMARY OF THE INVENTION

The present invention provides a process for the preparation of 1-hydroperoxy-16-oxabicyclo[10.4.0]hexadecane (DDP-OOH), wherein 13-oxabicyclo[10.4.0]hexadec-1(12)-ene (DDP) and hydrogen peroxide are reacted in a diluent in the presence of a strong acid, the diluent has a pKa value of greater than or equal to 4.5 and the strong acid has a pKa value of less than or equal to 1.5, wherein after the reaction has taken place, that is to say typically after the addition of the hydrogen peroxide has ended and after any subsequent after-reaction time, the strong acid is neutralized with at least 0.9 molar equivalent of a base.

DETAILED DESCRIPTION

The pKa value is understood as meaning the negative decimal logarithm of the acidity constant Ka in water at 25° C. (298 K): pKa=$-\log_{10}$ Ka. The pKa value is a measure of the strength of an acid.

Strong acids which have a pKa value of less than or equal to 1.0 are advantageous, and mineral acids and straight- or branched-chain fluorinated carboxylic acids are preferred here.

Preferred mineral acids are nitric acid, hydrochloric acid, perchloric acid and sulfuric acid, and sulfuric acid is particularly preferred. 50–98% strength by wt. sulfuric acids is in turn advantageous here.

Advantageous fluorinated carboxylic acids in the context of the present invention are straight- or branched-chain carboxylic acids, contain 2 to 6 carbon atoms, contain at least one fluorine atom and have a pKa value of less than or equal to 1.5. Highly fluorinated carboxylic acids or perfluorinated acids having a pKa value of less than or equal to 1.0 are preferred. In highly fluorinated carboxylic acids, at least 80%, preferably at least 90% of the hydrogen atoms of the C—H bonds are replaced by fluorine atoms. Preferred perfluorinated acids are trifluoroacetic acid, perfluoropropionic acid, perfluorobutanoic acid, perfluoropentanoic acid and perfluorohexanoic acid. Trifluoroacetic acid is very particularly preferred.

In addition, other strong acids, such as, for example, trifluoromethanesulfonic acid, can of course also be employed. Mixtures of strong acids can also be employed.

The preferred amount of strong acid, based on the DDP, is in the range from 0.1 to 10 mol %, particularly preferably in the range from 0.5 to 5 mol %.

Polar protic and polar aprotic diluents are particularly suitable diluents for the preparation of the DDP-OOH, and the diluents are advantageously liquid at 25° C. Polar protic diluents are preferred.

Advantageous diluents have a pKa value in the range of greater than or equal to 4.5 and less than or equal to 26. Preferred diluents have a pKa value in the range of greater than or equal to 4.5 and less than or equal to 18, particularly preferably one in the range of greater than or equal to 4.5 and less than or equal to 10.

Mixtures of diluents according to the invention can also be employed.

Organic acids, in particular straight- or branched-chain organic acids having 2 to 6 carbon atoms or mixtures of organic acids having 2 to 6 carbon atoms, are preferred. Acetic acid, propionic acid or a mixture of acetic acid and propionic acid are very particularly preferred diluents.

The weight ratio of DDP to diluent which is preferred according to the invention lies in the range from 1:1 to 1:8, preferably 1:2 to 1:4.

In addition to the diluent, the reaction medium advantageously additionally contains water. The weight ratio of DDP to water which is preferred according to the invention lies in the range from 10:1 to 1:1, preferably 5:1 to 2:1.

Before the DDP-OOH is employed in the fragmenting stage to give the 11(12)-pentadecen-15-olides, according to the invention the strong acid is neutralized with at least 0.9 molar equivalent of a base, preferably completely. Organic and inorganic bases, which can also be employed as a solution, can be used for the neutralization. Alkali metal hydroxides, alkaline earth metal hydroxides, alkali metal carbonates, alkaline earth metal carbonates and alkali metal or alkaline earth metal salts of a straight- or branched-chain organic acid having 1 to 6 carbon atoms are particularly preferred. Sodium hydroxide, potassium hydroxide, alkali metal acetate and alkali metal propionate are particularly preferred. Preferred alkali metal representatives are sodium and potassium.

The preferred amount of base, based on the strong acid, is at least 1.0 molar equivalent, and the amount is particularly preferably in the range from 1.0 to 2.5 molar equivalents, in particular in the range from 1.005 to 1.5 molar equivalents. Mixtures of bases can also be employed.

Hydrogen peroxide of varying content can be used for the addition of $H_2O_2$ on to DDP to give DDP-OOH. 10 to 70% strength by wt. aqueous hydrogen peroxide is typically employed, 30 to 55% strength by wt. is preferred, and 30% strength by wt. and 50% strength by wt. aqueous $H_2O_2$ are preferred.

The preferred amount of $H_2O_2$ is 0.9 to 2 molar equivalents, based on the DDP, and particularly preferably 1.2 to 1.6 molar equivalents.

The temperature range in which the addition of $H_2O_2$ is carried out is preferably −20 to +20° C., preferably −10 to +10° C. The temperature range can of course be chosen and optimized by the expert according to the diluent used. A temperature above +20° C. is preferably avoided, because the DDP-OOH formed is less stable at higher temperatures and increasingly decomposes as the temperature rises.

As similarly according to EP-A 424 787—OCP can also be used as the starting material for the preparation of DDP-OOH. Since water is formed during the cyclization to give DDP, it is advantageous to reduce the amount of water accordingly.

The DDP-OOH prepared by the process according to the invention is advantageously introduced without further working up or isolation, i.e. in the form of the crude reaction mixture, into the fragmenting stage to give the 11(12)-pentadecen-15-olides. The crude DDP-OOH reaction mixture is typically obtained in the form of a suspension. In view of the prior art, the fact that the process steps of isolation and/or washing to neutrality of the DDP-OOH are not necessary is particularly surprising.

The present invention also provides a process for the preparation of 11(12)-pentadecen-15-olides, in which a reaction mixture which has been obtained by the process according to the invention described above is employed without isolation of the DDP-OOH.

Cu(I) or Cu(II) compounds are advantageously employed for the fragmenting of the DDP-OOH contained in the reaction mixture.

The Cu(I) or Cu(II) compounds employed in the fragmenting of the DDP-OOH to give the 11(12)-pentadecen-15-olides in this context are advantageously those which, under the reaction conditions of the DDP-OOH reaction, are soluble to a certain extent in the high-boiling diluent used. Such copper compounds have solubility in the diluent at 20° C. of at least 0.5 g/kg of high-boiling diluent, preferably at least 1 g/kg. The copper compounds can be employed in anhydrous form or as hydrates (water of crystallization). The amount of water in the water of crystallization is not critical.

Cu(II) compounds are advantageous, and those with organic radicals are preferred. In addition to Cu(II) 2,4-pentanedionate derivatives, Cu(II) carboxylates are particularly suitable in this context. Preferred Cu(II) 2,4-pentanedionates are Cu(II) acetylacetonate, Cu(II) 1,1,1-trifluoroacetylacetonate and [bis(2,2,6,6-tetramethyl-3,5-heptanedionato)]-Cu(II). Cu(II) carboxylates of alkylcarboxylic acids having 2 to 5 carbon atoms, in particular Cu(II) acetate and Cu(II) propionate, are particularly preferred.

One or more copper compounds can be used according to the invention. The amount of the copper compounds which is advantageous according to the invention in the reaction of DDP-OOH to give the 11(12)-pentadecen-15-olides is 0.05 to 4 mol %, based on the DDP-OOH, particularly advantageously 0.1 to 2.5 mol %, preferably 0.1 to 1.5 mol % and particularly preferably 0.3 to 1.5 mol %, very particularly preferably 0.5 to 1.5 mol %.

Preferred high-boiling diluents for the reaction of the DDP-OOH to give the 11(12)-pentadecen-15-olides are polar and have a high boiling point, so that they remain in the reactor during the fragmenting reaction. The boiling point of the high-boiling diluent is thus preferably above the boiling point of the diluent used in the reaction stage for formation of the DDP-OOH, above the azeotropic mixture of diluent and water, and above the boiling point of the product, i.e. of the 11(12)-pentadecen-15-olides. High-boiling diluents having a boiling point of greater than or equal to 170° C. under a pressure of 5 mbar are therefore preferred.

It has furthermore been found that certain high-boiling diluents suppress precipitating out of copper and/or insoluble copper compounds during the cleavage. In this respect the reaction of DDP-OOH to give the 11(12)-pentadecen-15-olides is preferably carried out in the presence of high-boiling diluents which can be represented by the following formula:

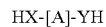

wherein

X and Y independently of one another denote O or N—R, wherein R=H or an organic radical having 1 to 10 carbon atoms, and A is an organic radical having up to 100 carbon atoms.

A preferably contains up to 50 carbon atoms, particularly preferably 10 to 30 carbon atoms. The radical R preferably contains 1 to 4 carbon atoms, and R is preferably methyl or ethyl. High-boiling diluents having a boiling point of greater than or equal to 170° C. under 5 mbar are also preferred here.

The organic radical A preferably contains the heteroatoms O or N, preferably in the form of hydroxyl groups, ether groups or amino groups, and ether groups and secondary amino groups are preferred. One or more organic groupings, which independently of one another can be straight-chain, branched, cyclic, heterocyclic, aromatic or heteroaromatic, preferred groups containing heteroatoms being those with O or N, can be attached to the carbon skeleton of the radical A.

Advantageous high-boiling diluents are α,ω-diols and α,ω-amino alcohols.

In a particularly advantageous embodiment, high-boiling diluents which contain exclusively oxygen as heteroatoms are employed. These α,ω-diols preferably contain at least 2 oxygen atoms, preferably in the form of ether groups, in the carbon skeleton of the organic radical A.

Polyalkylene glycols, in particular polyethylene glycols (PEG), polypropylene glycols or polytetramethylene glycols (polytetrahydrofurans) which have at least a boiling point of 170° C. under 5 mbar are particularly preferred high-boiling diluents. The polyalkylene glycols are polydisperse at higher molecular weights and have a molecular weight range, e.g. PEG 1000 typically has a molecular weight range of 950 to 1,050. Polyethylene glycols are very particularly preferred. PEG 400 to PEG 1500 are particularly preferred, and here in turn PEG 400, PEG 600, PEG 800 and PEG 1000. These products are commercially available.

One or more high-boiling diluents can be used according to the invention. The amount of high-boiling diluent which is advantageous according to the invention in the reaction of DDP-OOH to give the 11(12)-pentadecen-15-olides is 5 to 100 wt. %, based on the DDP-OOH, preferably 10 to 70 wt. %, particularly preferably 15 to 60 wt. % and very particularly preferably 20 to 50 wt. %.

The temperature range in which the cleavage is carried out is advantageously in the range from 70 to 120° C. The cleavage is preferably carried out at temperatures in the range from 85 to 110° C., particularly preferably at 90 to 100° C.

The advantageous pressure range in which the fragmenting of the DDP-OOH is carried out is 0.01 mbar to 2 bar. The process is preferably carried out under pressures below 1,013 mbar, in particular in the range from 50 to 800 mbar.

The fragmenting is advantageously carried out by adding the DDP-OOH suspension dropwise to a mixture of the copper compound and the high-boiling diluent.

The low amounts of waste are a further advantage of the process. No waste water is produced in the process, and the solvent used in the preparation of DDP-OOH can be sluiced into the process again after distillation. This is particularly advantageous from environmental and economic aspects.

Isolated yields of 11(12)-pentadecen-15-olides of about 87% of th. of 11(12)-pentadecen-15-olides (sum of the various isomers) can be achieved by the process according to the invention. In addition, about 1–2% pentadecan-15-olide and 5–7% DDP, which can be sluiced into the process again, are typically obtained.

EXAMPLES

General Construction of the Experiments

The experiments were carried out in double-walled stirred reactors which were temperature-controlled via a cryostat or thermostat. The bottom outlet of the reactor in which the preparation of the hydroperoxide took place was connected via a hose pump to a metering line of the fragmenting reactor.

Example 1

633 g (2.85 mol) DDP, 1,800 g propionic acid, 180 g water and 15 g trifluoroacetic acid are brought together in the first reactor and cooled to −10° C. 265 g of a 50% strength by wt. aqueous solution of hydrogen peroxide are added dropwise at −10 to +10° C. An after-reaction time of 1 hour, during which the hydroperoxide crystallizes, follows. 53 g of a 10% strength by wt. sodium hydroxide solution are then added.

The suspension formed is conveyed in the course of 3 hours into the fragmenting reactor, into which 200 g polydiol 400 and 4 g copper(II) acetate monohydrate have been initially introduced at 90° C. A propionic acid/water mixture is distilled off here.

The crude product obtained in this manner gives, after distillation over a 30 cm packed column, 665 g of distillate which comprises 89 wt. % 11(12)-pentadecen-15-olides (sum of the various isomers; the isomers are present to the extent of about 40%, 27% and 22%), 2 wt. % pentadecan-15-olide and 5 wt. % DDP. This corresponds to a yield of 87% of theory of 11(12)-pentadecen-15-olide (sum of the isomers).

Example 2

633 g (2.85 mol) DDP, 1,800 g propionic acid, 180 g water and 15 g trifluoroacetic acid are brought together in the first reactor and cooled to −10° C. 245 g of a 50% strength by wt. aqueous solution of hydrogen peroxide are added dropwise at −10 to +10° C. An after-reaction time of 1 hour, during which the DDP-OOH crystallizes, follows. 65 g of 23% strength by wt. sodium propionate solution are then added.

The suspension formed is conveyed in the course of 3 hours into the fragmenting reactor, into which 200 g polydiol 400 and 4 g copper(II) acetate monohydrate have been initially introduced at 90° C. A propionic acid/water mixture is distilled off here.

The crude product obtained in this manner gives, after distillation over a 30 cm packed column, 662 g of distillate which comprises 81 wt. % 11(12)-pentadecen-15-olide (sum of the various isomers), 1 wt. % pentadecan-15-olide and 7 wt. % DDP. This corresponds to a yield of 80% of th. of 11(12)-pentadecen-15-olide (sum of the various isomers; the isomers are present to the extent of about 40%, 27% and 22%).

Example 3

633 g (2.85 mol) DDP, 1,800 g propionic acid, 180 g water and 6.6 g concentrated sulfuric acid (96% strength) are brought together in the first reactor and cooled to −10° C. 245 g of a 50% strength by wt. aqueous solution of hydrogen peroxide are added dropwise at −10 to +10° C. An after-reaction time of 1 hour, during which the hydroperoxide crystallizes, follows. 63 g of a 10% strength by wt. sodium hydroxide solution are then added.

The suspension formed is conveyed in the course of 3 hours into the fragmenting reactor, into which 200 g polydiol 400 and 4 g copper(II) acetate monohydrate have been initially introduced at 90° C. A propionic acid/water mixture is distilled off here.

The crude product obtained in this manner gives, after distillation over a 30 cm packed column, 663 g of distillate which comprises 88 wt. % 11(12)-pentadecen-15-olide (sum of various isomers), 1 wt. % pentadecan-15-olide and 3 wt. % DDP. This corresponds to a yield of 86% of th. of 11(12)-pentadecen-15-olide (sum of the various isomers; the isomers are present to the extent of about 40%, 27% and 22%).

What is claimed is:

1. A process for the preparation of a reaction mixture containing 1-hydroperoxy-16-oxabicyclo[10.4.0]hexadecane (DDP-OOH), said process comprising:
    reacting 13-oxabicyclo[10.4.0]hexadec-1(12)-ene (DDP) and hydrogen peroxide in a diluent having a pKa value of greater than or equal to 4.5 and a strong acid having a pKa value of less than or equal to 1.5; and
    neutralizing the strong acid with at least 0.9 molar equivalent of a base, to produce said reaction mixture containing 1-hydroperoxy-16-oxabicyclo[10.4.0]hexadecane (DDP-OOH).

2. The process according to claim 1, wherein the diluent has a pKa value in the range of greater than or equal to 4.5 and less than or equal to 25.

3. The process according to claim 1, wherein the diluent is a straight- or branched-chain organic acid having 2 to 6 carbon atoms or a mixture of organic acids having 2 to 6 carbon atoms.

4. The process according to claim 1, wherein the diluent is acetic acid, propionic acid or a mixture of acetic acid and propionic acid.

5. The process according to claim 1, wherein the strong acid has a pKa value of less than or equal to 1.0.

6. The process according to claim 1, wherein the strong acid is a mineral acid or a straight- or branched-chain fluorinated carboxylic acid.

7. The process according to claim 1, wherein the strong acid is chosen from the group consisting of sulfuric acid, trifluoroacetic acid, perfluoropropionic acid, perfluorobutanoic acid, perfluoropentanoic acid and perfluorohexanoic acid.

8. The process according to claim 1, wherein an aqueous hydrogen peroxide solution having a hydrogen peroxide content in the range from 10 to 75 wt.% is employed.

9. The process according to claim 1, wherein the base is chosen from the group consisting of alkali metal hydroxide, alkaline earth metal hydroxide and alkali metal or alkaline earth metal salt of a straight- or branched-chain organic acid having 1 to 6 carbon atoms.

10. The process according to claim 1, wherein the base is chosen from the group consisting of sodium hydroxide, potassium hydroxide, alkali metal acetate and alkali metal propionate.

11. A reaction mixture containing 1-hydroperoxy-16-oxabicyclo[10.4.0]hexadecane (DDP-OOH) obtained by a process comprising:
reacting 13-oxabicyclo[10.4.0]hexadec-1(12-ene (DDP) and hydrogen peroxide in a diluent having a pKa value of greater than or equal to 4.5 and a strong acid having a pKa value of less than or equal to 1.5; and
neutralizing the strong acid with at least 0.9 molar equivalent of a base.

12. A process for the preparation of 11(12)-pentadecen-15-olide from 1-hydroperoxy-16-oxabicyclo[10.4.0]hexadecane (DDP-OOH), said process comprising:
dissolving a copper compound in a high-boiling diluent;
heating and, optionally, reducing the pressure over the high-boiling diluent solution;
adding a reaction mixture containing 1-hydroperoxy-16-oxabicyclo[10.4.0]hexadecane (DDP-OOH), resulting from reacting 13-oxabicyclo[10.4.0]hexadec-1(12)-ene (DDP) and hydrogen peroxide in a diluent having a pKa value of greater than or equal to 4.5 and a strong acid having a pKa value of less than or equal to 1.5 and neutralizing the strong acid with at least 0.9 molar equivalent of a base, to the high-boiling diluent solution; and
concentrating or isolating the 11(12)-pentadecen-15-olide.

13. The process according to claim 12, wherein the copper compound has a solubility in the high-boiling diluent at 20° C. of at least 0.5 g/kg of high-boiling diluent.

14. The process according to claim 13, wherein the high boiling diluent has at least a boiling point of 170° C. under 5 mbar.

15. The process according to claim 13 wherein the high boiling diluent is chosen from one or more compounds of the formula:

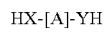

wherein
X and Y independently of one another denote 0 or N—R, wherein R=H or an organic radical having 1 to 10 carbon atoms, and
A is an organic radical having up to 100 carbon atoms.

16. The process according to claim 12, wherein the diluent is an organic acid.

17. The process according to claim 6, wherein the strong acid is a perfluorinated carboxylic acid.

18. The process according to claim 8, wherein an aqueous hydrogen peroxide solution having a hydrogen peroxide content in the range from 30 to 55 wt.% is employed.

* * * * *